(12) United States Patent
Pape

(10) Patent No.: US 6,530,868 B1
(45) Date of Patent: Mar. 11, 2003

(54) EXERCISE DEVICE

(76) Inventor: Leslie Pape, 14131 Baroness Ct., Orlando, FL (US) 32828

( * ) Notice: Subject to any disclaimer, the term of this patent is extended or adjusted under 35 U.S.C. 154(b) by 0 days.

(21) Appl. No.: 09/535,845

(22) Filed: Mar. 27, 2000

(51) Int. Cl.⁷ .............................................. A63B 21/00
(52) U.S. Cl. ...................... 482/112; 482/124; 482/127
(58) Field of Search ............................ 602/16, 23, 26; 482/124, 127, 74, 80, 44; 2/112

(56) References Cited

U.S. PATENT DOCUMENTS

| | | |
|---|---|---|
| 1,432,013 A | 10/1922 | Blake |
| 2,035,010 A | 3/1936 | Rawlings |
| 3,162,441 A | 12/1964 | Karlik |
| 3,999,752 A | 12/1976 | Kupperman et al. |
| 4,271,831 A | 6/1981 | Deibert |
| 4,433,679 A * | 2/1984 | Mauldin et al. ............ 482/124 |
| 4,441,707 A | 4/1984 | Bosch |
| 4,540,173 A | 9/1985 | Hopkins, Jr. |
| 4,606,542 A * | 8/1986 | Segal et al. .................... 602/23 |
| 4,685,671 A | 8/1987 | Hagerman et al. |
| 4,768,500 A | 9/1988 | Mason et al. |
| 4,911,439 A | 3/1990 | Kuhl |
| 5,042,799 A * | 8/1991 | Stanley ........................ 482/124 |
| 5,328,446 A * | 7/1994 | Bunnell et al. ................ 602/16 |
| 5,358,468 A * | 10/1994 | Longo et al. .................. 601/33 |
| 5,456,268 A * | 10/1995 | Bonutti ........................ 602/16 |
| 5,472,412 A * | 12/1995 | Knoth .......................... 602/26 |

FOREIGN PATENT DOCUMENTS

| | | |
|---|---|---|
| GB | 20463 | 9/1907 |
| GB | 245274 | 1/1925 |

* cited by examiner

*Primary Examiner*—Jerome Donnelly
(74) *Attorney, Agent, or Firm*—Reising, Ethington, Barnes, Kisselle, Learman and McCulloch, P.C.

(57) ABSTRACT

An exercise device for a person. The exercise device includes mounting straps for mounting on each of two body members on opposite sides of a selected joint of the person, a support member connected to each mounting strap, and a resistance mechanism interconnecting the support members for exercising at least one of the two body members upon repeated moving at least one of the members. The selected joint comprises one of a knee, a hip, an ankle, a wrist, an elbow, and a shoulder. The resistance mechanism includes one of a damper and a pulley with associated rubber bands connected to the oppositely disposed support members.

5 Claims, 5 Drawing Sheets

EXERCISE DEVICE

BACKGROUND OF THE DISCLOSURE

1. Technical Field

This invention relates generally to exercise devices and, more particularly, to such a device worn by a user for flexing the user's upper body muscles, for example, the muscles in the shoulders, hips, upper arms, lower arms, upper legs, lower legs, ankles and wrists.

2. Background Art

Tolle U.S. Pat. No. 4,993,705 discloses an athletic device for the upper body, including a vest, and a elastically expandable strap fastened in place in an X-configuration across a back part of the vest and extended over the user's shoulders to terminate with two lower arm or wrist cuffs.

Kuhl U.S. Pat. No. 4,911,439 discloses a resilient exercise apparatus including a pair of loops made of a single length of elastic cord to form generally figure eight shape, and mounted over the shoulders and around the waist of the user, with a tubular handle mounted on each front and side sections of the cord.

Karlik U.S. Pat. No. 3,162,441 discloses an exercise devise including a frame for mounting on the back or chest of a user via upper and lower belts, three springs and a plurality of pulleys on the frame to accommodate a flexible cord with two stirrups.

British patent number 245,274 discloses an exercise device including a belt adapted to be secured around the waist or to be hung over the shoulders of the user, with elastic cords attached via springs to the belt, with hand grips at the ends thereof.

Exercise devices associated with waist belts and hand grips and/or wrist cuffs are shown and described in the following U.S. Pat. Nos.: Davies U.S. Pat. No. 5,433,688; Hagerman et al U.S. Pat. No. 4,685,671; Hopkins U.S. Pat. No. 4,540,173; Bosch U.S. Pat. No. 4,441,707; Kupperman et al U.S. Pat. No. 3,999,752; Rawlings U.S. Pat. No. 2,035,010; and Blake U.S. Pat. No. 1,432,013; and British patent number 20,463.

Each of Bastyr et al U.S. Pat. No. 5,292,303; Delbert U.S. Pat. No. 4,271,831 and Nebolon U.S. Pat. No. 5,409,449 disclose orthopedic braces hinged at the knee joint of the wearer for free but adjustably limited knee movement. Gildersleeve U.S. Pat. No. 5,316,547 discloses an orthopedic brace having medial and lateral knee hinges, with pneumatic pads for positioning against the body of a user. Mason et al U.S. Pat. No. 4,768,500 discloses an discloses an athletic knee protector with upper and lower leaf spring members interconnected by gear teeth pivotally engaged between a pair of plates.

DISCLOSURE OF THE INVENTION

A general object of the invention is to provide an improved exercise device worn by a user to exercise body parts, such as muscles, adjacent his or her shoulder, hip, knee, ankle, elbow and/or wrist joints.

Another object of the invention is to provide such exercise devices, which utilize upper and lower extensions with an intermediate damper for use on body parts straddling various body joints.

A further object of the invention is to provide an alternate exercise is arrangement including a pulley and rubber bands in lieu of a damper for use adjacent various body joints.

These and other objects and advantages will become more apparent when reference is made to the following drawings and the accompanying description.

BEST MODE FOR CARRYING OUT THE INVENTION

Figure 1:
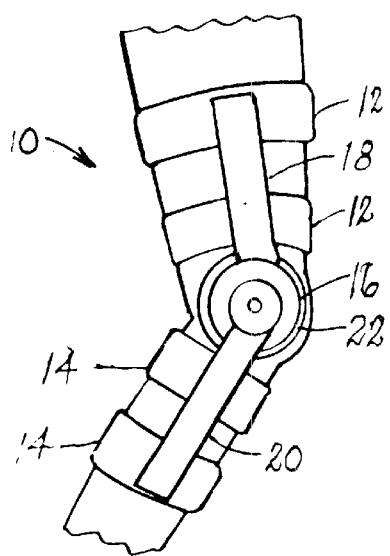
FIG. 1 is a side elevational view of the inventive exercise device adapted to being used on oppositely disposed body parts adjacent a knee joint.

Referring now to the drawings in greater detail, FIG. 1 illustrates an exercise device 10 for use on a user's leg, including either one or a pair of spaced-apart upper support straps 12, secured around one's leg above the knee joint by any suitable means, such as buckle, snap connector, or Velcro fastening (not shown); either one or a pair of spaced-apart lower support straps 14 secured below the knee joint; a resistance mechanism in the form of a damper 16 adjacent the user's knee joint; an upper swing arm 18 attached to both upper straps 12 and to the damper 16; a lower swing arm 20 attached to both lower straps 14 and to the damper 16; and a cushion pad 22 secured to the inner surface of the damper 16 so as to be positioned between the damper 16 and the knee. As will be explained, the damper 16 serves to provide a resistance to each repeated bending and straightening movement about the knee joint.

Figure 2:
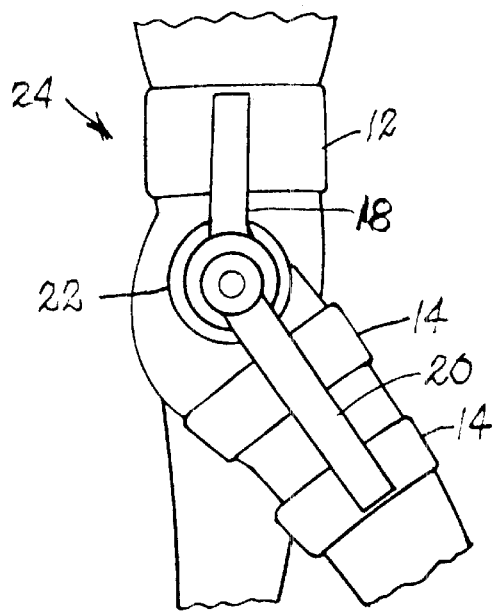
FIG. 2 is a side elevational view of the inventive exercise device adapted to being used on oppositely disposed body parts adjacent a hip joint.

In FIG. 2, an exercise device 24 includes the same elements as in FIG. 1, but with a single upper strap 12 mounted around a user's waist and either one or a pair of straps 14 around an upper leg portion, so as to position the damper 16 and the cushion pad 22 adjacent a hip joint.

Figure 3:
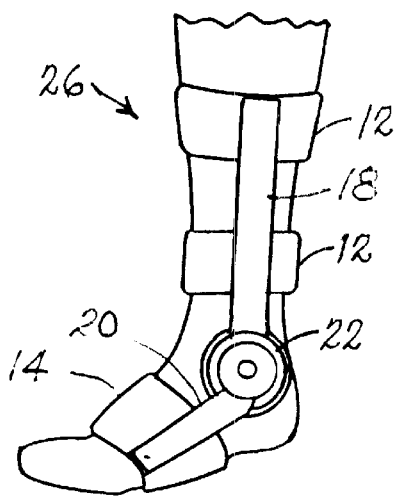
FIG. 3 is a side elevational view of the inventive exercise device adapted to being used on oppositely disposed body parts adjacent an ankle joint.

In FIG. 3, an exercise device 26 likewise includes the same elements as in FIG. 1, but mounted around a user's ankle and a single support strap 14 mounted around the user's foot with the damper 16 positioned adjacent an ankle joint.

Figure 4:
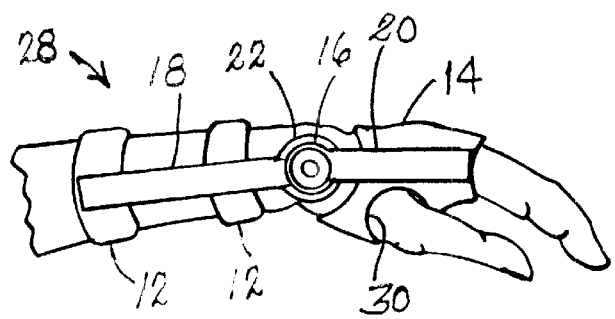
FIG. 4 is a side elevational view of the inventive exercise device adapted to being used on oppositely disposed body parts adjacent a wrist joint.

In FIG. 4, an exercise device 28 includes a pair of support straps 12 around a wrist and a contoured strap 14 with a thumb hole 30 formed therein and mounted around a user's hand with the damper 16 and cushion pad 22 positioned adjacent the wrist joint.

Figure 5:
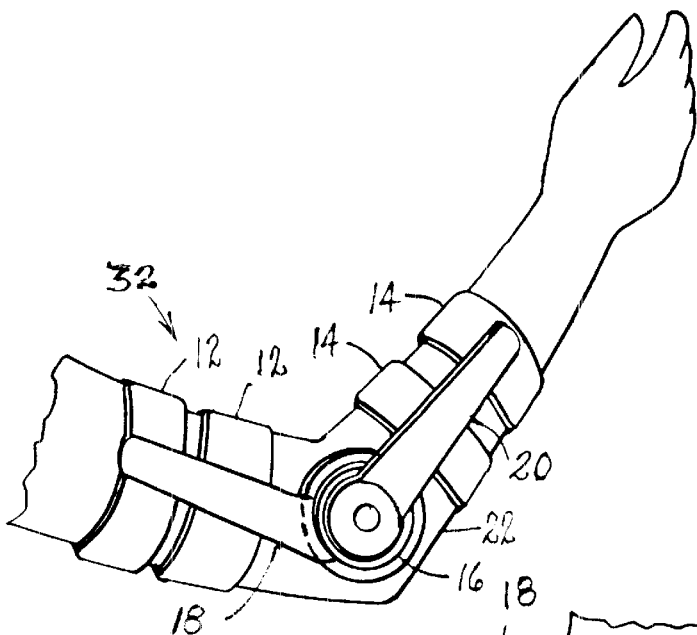
FIG. 5 is a side elevational view of the inventive exercise device adapted to being used on oppositely disposed body parts adjacent an ankle joint.

In FIG. 5, an exercise device 32 is similar to the FIG. 1 exercise 10 but mounted relative to an elbow joint.

Figure 6:
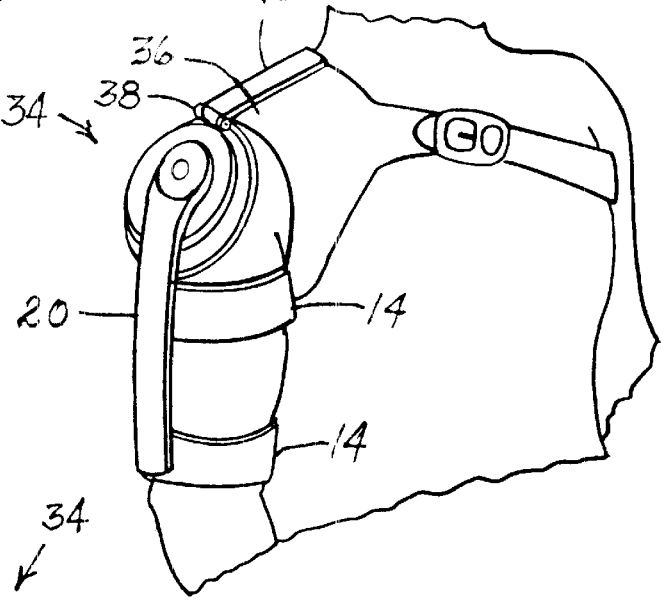
FIG. 6 is a front perspective view of the inventive exercise device adapted to used on oppositely disposed body parts adjacent a shoulder joint.
Figure 7:
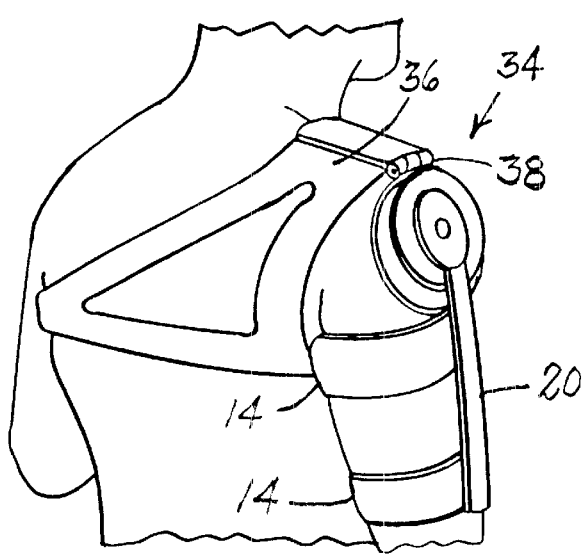
FIG. 7 is a rear perspective view of the inventive exercise device adapted to being used on oppositely disposed body parts adjacent a shoulder joint.

FIGS. 6 and 7 disclose an exercise device 34 adaptable to a shoulder joint. The device 34 includes a right or left hand shoulder strap 36 wrapped around the wearer's back, chest and opposite arm pit, connected together on the chest by any suitable means, such as a snap buckle 38. The upper swing arm 18 is secured to the shoulder strap 36 along the shoulder, with the outer end thereof connected by a suitable hinge 40 to an edge of the damper 16. The lower swing arm 20 extends downwardly from an outer surface of the damper 16 to the two lower support straps 14 spaced-apart around the user's upper arm. The cushion pad 22 is adjacent the damper 16 against the upper arm surface adjacent the shoulder.

Figure 8:
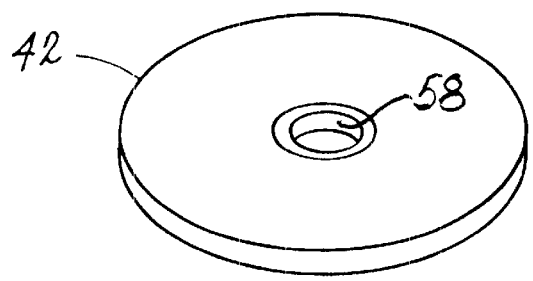
FIG. 8 is a perspective view of a lid of a rotary damper.
Figure 9:
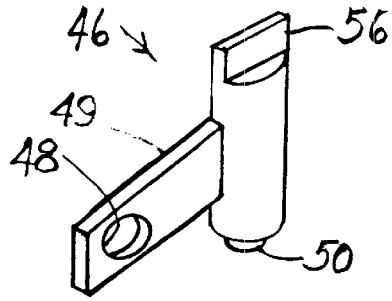
FIG. 9 is a perspective view of an impeller of a rotary damper.
Figure 10:
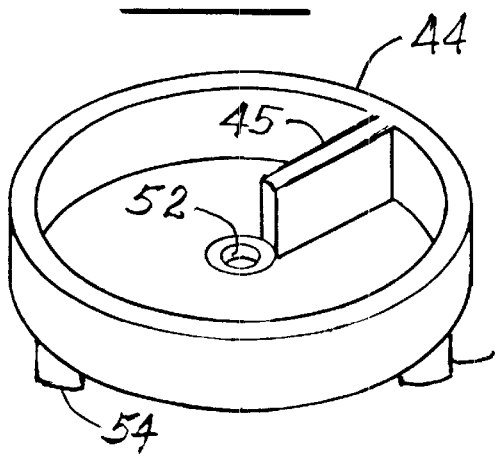
FIG. 10 is a perspective view of a base of a rotary damper.

Referring now to FIGS. 8 through 10, there are disclosed three elements which form the damper 16. Specifically, the damper 16 includes a lid 42 for mounting on a base 44 including a radially extending inner wall 45, enclosing an impeller 46 having a predetermined opening 48 formed in a radially extending vane 49, and rotatable in a selected viscous fluid (not shown) such as a silicone of a predetermined viscosity. The viscosity thereof and/or opening size in the vane may be varied to increase or decrease the damping torque in cooperation with the back and forth flow of the fluid through the opening 48 limited only by the engagement of the vane 49 against a side of the wall 45. One formed end 50 of the impeller 46 is pivotally mounted in an impeller bearing hole 52 formed in the bottom inner surface of the base 44. Location lugs 54 on an outer surface of the base 44 are secured in any suitable manner to one end of one of the upper and lower swing arms 18 and 20. A location connector 56 is formed at the other end of the impeller to extend through a sealed bearing hole 58 formed in the center of the lid 42, for connection in any suitable manner to the other of the ends of the lower or upper swing arms 20 and 18 of each assembly.

Figure 11:
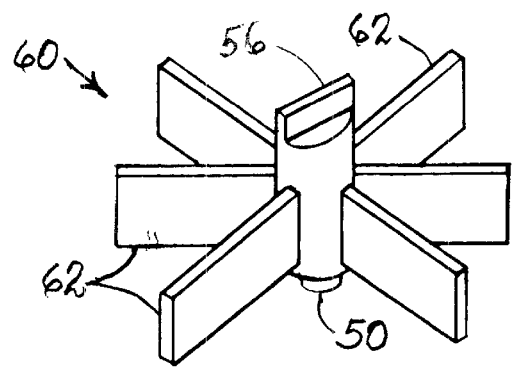
FIG. 11 is a perspective view of an alternate impeller of a rotary damper.
Figure 12:
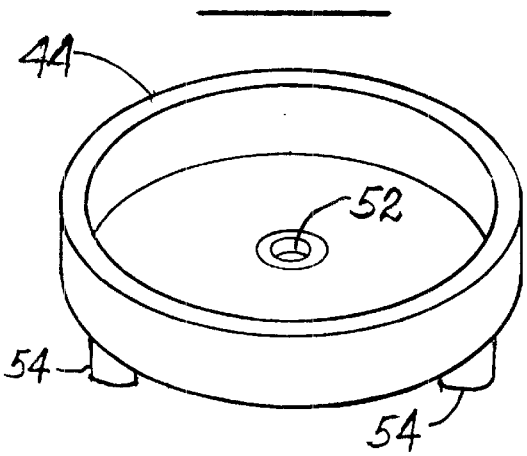
FIG. 12 is a perspective view of a base of the FIG. 11 rotary damper.
Figure 13:
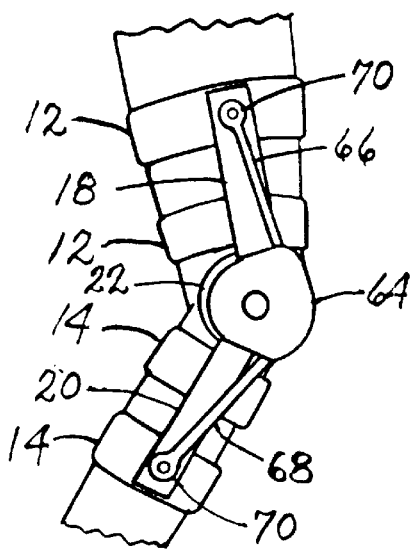
FIG. 13 is a side elevational view of the alternate inventive exercise device adapted to being used on oppositely disposed body parts adjacent a knee joint.
Figure 14:
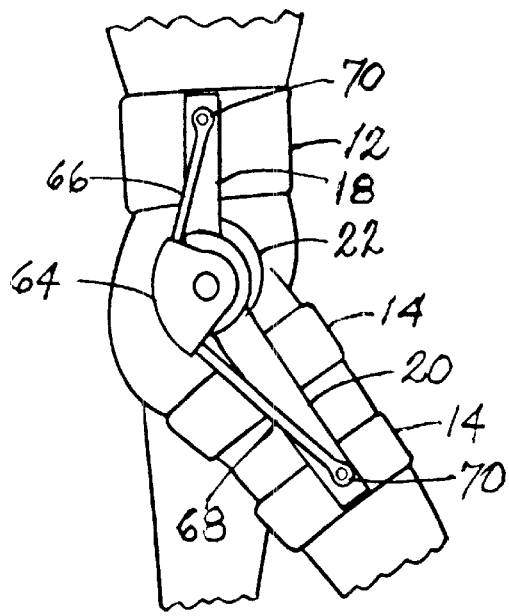
FIG. 14 is a side elevational view of the alternate inventive exercise device adapted to being used on oppositely disposed body parts adjacent a hip joint.
Figure 15:
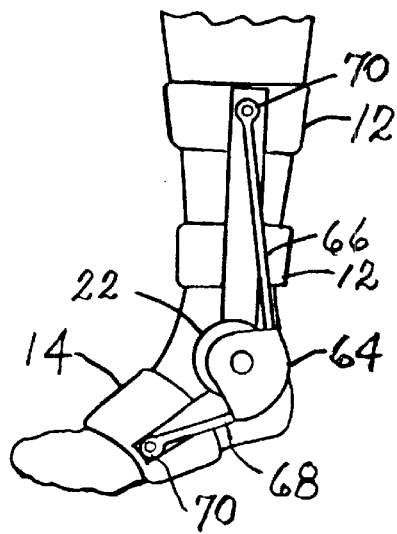
FIG. 15 is a side elevational view of the alternate inventive exercise device adapted to being used on oppositely disposed body parts adjacent an ankle joint.
Figure 16:
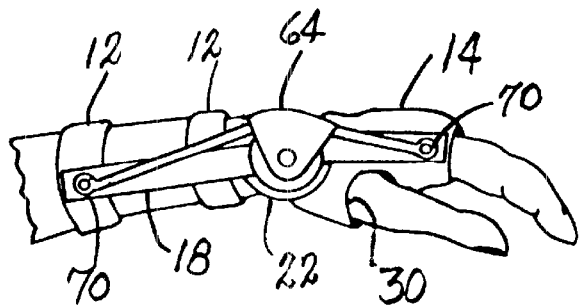
FIG. 16 is a side elevational view of the alternate inventive exercise device adapted to being used on oppositely disposed body parts adjacent a wrist joint.
Figure 17:
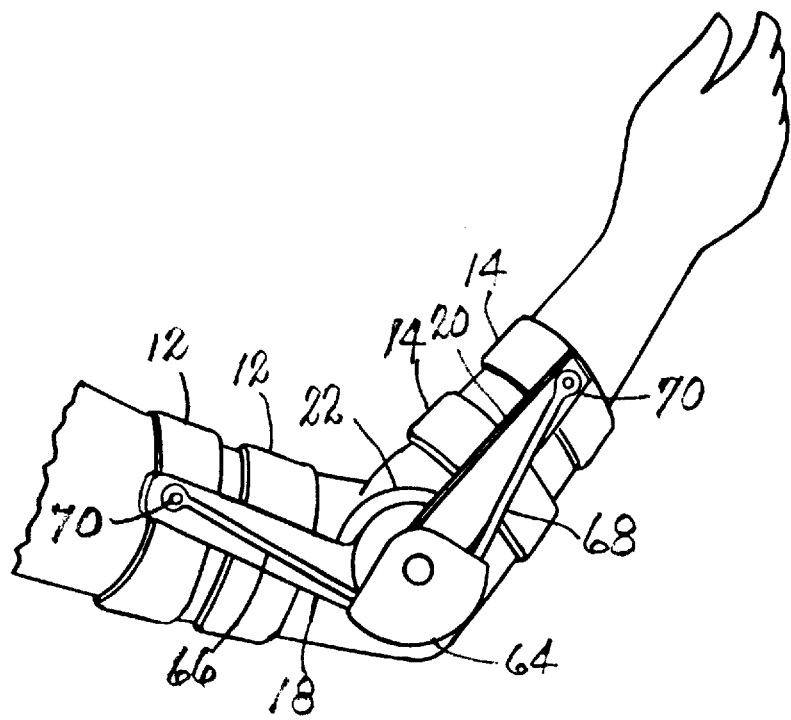
FIG. 17 is a side elevational view of an alternate inventive exercise device adapted to being used on oppositely disposed body parts adjacent an elbow joint.
Figure 18:
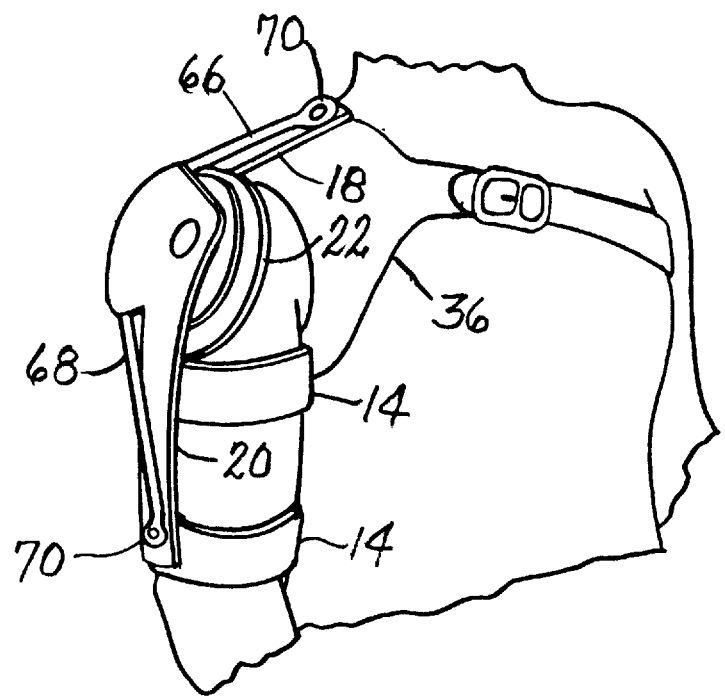
FIG. 18 is a front perspective view of the alternate exercise device adapted to being used on oppositely disposed body parts adjacent a shoulder joint.

As shown in FIGS. 11 and 12, an impeller 60 to includes six vanes 62 in lieu of the perforated vane 49, and a base 44 with no inner wall 45. The vanes 62 and the inside diameter of the base 44 are each sized as desired to increase or decrease the rotary damping torque.

FIGS. 13, 14, 15, 16, 17 and 18 are comparable to FIGS. 1, 2, 3, 4, 5 and 6, respectively, except that the damper 16 is replaced with a covered pulley 64 or other covered arcuate shaped element having an elastomeric member, such as a rubber band having oppositely disposed end portions 66 and 68, extending therearound and along respective upper and lower swing arms 18 and 20, and being connected at the respective, distal ends thereof by suitable studs 70. The pulley 64 may be a simple pulley wheel, with the rubber band 66, 68 looped around a portion thereof. Alternately, the rubber band 66, 68 may simply slide along a fixed arcuate shaped surface.

In operation, movements of one's upper and lower arm, hand, upper or lower leg and foot, with the exercise device in place, serves to exercise these body members and their associated joints.

It should be apparent that the invention provides an improved exercise device for exercising virtually every muscle group adjacent all body joints.

What is claimed is:

1. An exercise device for a person, said exercise device comprising at least one mounting strap for mounting on each of two body members on upper and lower sides of a selected joint of the person, a single support member connected to each mounting strap, and a resistance means in the form of a damper assembly, interconnecting said support members for exercising at least one of the two body members upon moving at least one of said members;

wherein said damper assembly includes a base member secured to one of said mounting straps; a lid having a central hole formed therein; and an intermediate impeller pivotally mounted at one end thereof in said base member, and having the other end thereof extended through a bearing in said central hole and secured to the other of said mounting straps; and a selected viscous fluid confined between said member and said lid for providing a predetermined damping torque in cooperation with clockwise and counterclockwise rotary movement of the impeller by the user's body member.

2. The exercise device described in claim 1, wherein said selected joint comprises one of a knee, a hip, an ankle, a wrist, an elbow and a shoulder.

3. The exercise device described in claim 1, wherein said impeller includes a single perforated vane pivotally reversibly operable in said viscous fluid.

4. The exercise device described in claim 1, wherein said impeller includes a plurality of equally spaced, radially extending vanes sized as required within said base so as to control the damping torque of said viscous fluid during pivotal operation of said vanes.

5. An exercise device for a person, said exercise device comprising at least one mounting strap for mounting on each of two body members on upper and lower sides of a selected joint of the person, a single support member connected to each mounting strap, and resistance means interconnecting said support members for exercising at least one of the two body members upon moving at least one of said members, wherein said selected joint comprises one of a knee, a hip, an ankle, a wrist, an elbow and a shoulder, and wherein said resistance means is a damper assembly;

wherein said damper assembly includes a base member secured to one of said mounting straps; a lid having a central hole formed therein; and an intermediate impeller pivotally mounted at one end thereof in said base member, and having the other end thereof extended through a bearing in said central hole and secured to the other of said mounting straps; and a selected viscous fluid confined between said member and said lid for providing a predetermined damping torque in cooperation with clockwise and counterclockwise rotary movement of the impeller by the user's body member.

* * * * *

UNITED STATES PATENT AND TRADEMARK OFFICE
CERTIFICATE OF CORRECTION

PATENT NO. : 6,530,868 B1  Page 1 of 1
DATED : March 11, 2003
INVENTOR(S) : Leslie Pape It is certified that error appears in the above-identified patent and that said Letters Patent is hereby corrected as shown below:

Column 1,
Line 8, after "user's" delete "upper body"
Line 50, before "athletic knee" delete "discloses an"
Line 66, after "exercise" delete "is"

Column 2,
Line 24, after "adapted to" insert therein -- being --

Column 3,
Line 58, after "60" delete "to"

Signed and Sealed this

Twenty-seventh Day of April, 2004

JON W. DUDAS
*Acting Director of the United States Patent and Trademark Office*